US012781256B2

(12) United States Patent
Slotsbo

(10) Patent No.: US 12,781,256 B2
(45) Date of Patent: Nov. 3, 2026

(54) METHOD AND A SYSTEM FOR DETERMINING SUSCEPTIBILITY

(71) Applicant: Pro Devices A/S, Hilleroed (DK)

(72) Inventor: Per Slotsbo, Vaerloese (DK)

(73) Assignee: Pro Devices A/S, Hilleroed (DK)

( * ) Notice: Subject to any disclaimer, the term of this patent is extended or adjusted under 35 U.S.C. 154(b) by 825 days.

(21) Appl. No.: 17/917,103

(22) PCT Filed: Apr. 7, 2021

(86) PCT No.: PCT/EP2021/059030
§ 371 (c)(1),
(2) Date: Oct. 5, 2022

(87) PCT Pub. No.: WO2021/204854
PCT Pub. Date: Oct. 14, 2021

(65) Prior Publication Data

US 2023/0151403 A1 May 18, 2023

(30) Foreign Application Priority Data

Apr. 7, 2020 (EP) .................................... 20168457

(51) Int. Cl.

| | |
|---|---|
| ***C12Q 1/18*** | (2006.01) |
| ***C12M 1/34*** | (2006.01) |
| ***G06T 7/00*** | (2017.01) |
| ***G06T 7/13*** | (2017.01) |
| ***G06T 7/62*** | (2017.01) |
| ***G06T 7/73*** | (2017.01) |

(52) U.S. Cl.
CPC ............... *C12Q 1/18* (2013.01); *C12M 41/36* (2013.01); *G06T 7/0012* (2013.01); *G06T 7/13* (2017.01); *G06T 7/62* (2017.01); *G06T 7/73* (2017.01); *G06T 2207/30024* (2013.01); *G06T 2207/30096* (2013.01)

(58) Field of Classification Search
None
See application file for complete search history.

(56) References Cited

U.S. PATENT DOCUMENTS

| | | | |
|---|---|---|---|
| 3,780,223 | A | 12/1973 | Perry |
| 6,153,400 | A | 11/2000 | Matsumura et al. |
| 6,696,269 | B2 | 2/2004 | Newell |
| 2003/0186350 | A1 | 10/2003 | Newell |

FOREIGN PATENT DOCUMENTS

| | | | | | |
|---|---|---|---|---|---|
| CN | 108 053 442 | A | | 5/2018 | |
| EP | 1002050 | A1 | | 5/2000 | |
| EP | 1016707 | A2 | | 7/2000 | |
| EP | 1198587 | A1 | | 4/2002 | |
| GB | 2344419 | A | * | 6/2000 | ............... G06T 7/62 |
| WO | WO9902645 | | * | 1/1999 | |
| WO | WO-01/09371 | A1 | | 2/2001 | |
| WO | WO-2019063690 | A1 | * | 4/2019 | ............... C12Q 1/18 |

OTHER PUBLICATIONS

Hejblum, G. et al. 1993. Automated interpretation of disk diffusion antibiotic susceptibility tests with the radial profile analysis algorithm. Journal of Clinical Microbiology 31(9): 2396-2401; specif. pp. 2396, 2397 (Year: 1993).*
Bhargav, H.S. et al. 2016. Measurement of the zone of inhibition of an antibiotic. 2016 IEEE 6th International Conference on Advanced Computing, pp. 409-414; specif. pp. 410, 412 (Year: 2016).*
Diab, A. et al. 2017. Automatic reading and interpretation of an antibiogram. Fourth International Conference on Advances in Biomedical Engineering, pp. 1-4; specif. pp. 1, 2, 3 (Year: 2017).*
LFR Costa et al.: “Development of an automatic identification algorithm for antibiogram analysis”, Computers in Biology and Medicine, New York, NY, US, vol. 67, Oct. 20, 2015, pp. 104-115.
A Diab et al.: “Automatic reading and interpretation of an antibiogram”, 2017 Fourth International Conference on advances in biomedical engineering (ICABME), IEE, Oct. 19, 2017, pp. 1-4.
A Gavoille et al.: “Measurement of inhibition zone diameter in disk susceptibility tests by computerized image analysis”, Computers in biology and Medicine, New York, NY, US, vol. 24, No. 3, May 1, 1994, pp. 179-188.
G Hejblum et al.: “Automated Interpretation of Disk Diffusion Antibiotic Susceptibility Tests with the Radia Profile Analysis Algorith”, Journal of Clinical Microbiology, American Society for Microbiology, US, vol. 31, No. 9, Sep. 1, 1993, pp. 2396-2401.
M Duman et al.: “Automatic Identification and Measurement of Antibiogram Analysis”, Jul. 31, 2019, Retrieved from the Internet: URL: <http://earsiv.cankaya.edu.tr:8080/xmlui/bitstream/handle/20.500.12416/3472/Duman,%20Merve.pdf?sequence=1&isAllowed=y>.
International Search Report for International Application No. PCT/EP2021/059030 dated May 31, 2021.
Written Opinion for International Application No. PCT/EP2021/059030 dated May 31, 2021.

* cited by examiner

*Primary Examiner* — Blaine Lankford
(74) *Attorney, Agent, or Firm* — Harness, Dickey & Pierce, P.L.C.

(57) ABSTRACT

In a susceptibility test, such as an antibiotic susceptibility test, an image is made of the carrier with the medium with the elements thereon, where circles are provided around the circles. The radii of the circles are determined to determine the susceptibility.

8 Claims, 1 Drawing Sheet

METHOD AND A SYSTEM FOR DETERMINING SUSCEPTIBILITY

CROSS-REFERENCE TO RELATED APPLICATIONS

This application is a national phase under 35 U.S.C. § 371 of PCT International Application No. PCT/EP2021/059030 which has an International filing date of Apr. 7, 2021, which claims priority to European Patent Application No. 20168457.8, filed Apr. 7, 2020, the entire contents of each of which are hereby incorporated by reference.

The present invention relates to the determination of susceptibility and in particular microbial/bacterial antibiotic susceptibility using imaging.

Relevant technology may be seen in: EP1002050, U.S. Pat. No. 6,153,400, EP1198587, EP1016707, U.S. Pat. Nos. 3,780,223, 6,696,269, US2003/0186350, and WO01/09371.

In a first aspect, the invention relates to a method of determining susceptibility, the method comprising:

- providing a carrier with:
  - a medium comprising one of
    - bacteria, micro organism or cells or
    - a composition affecting the bacteria or cells
  - a plurality of elements each comprising the other of the composition or the bacteria/cells, at least a portion of an outline formed around at least one element,
- providing an image of the carrier with the plurality of elements, the image having a number of pixels each having a pixel value,
- determining a diameter of the outline of at least one element by:
  - in a plurality of directions from a centre of the element:
    - determining a change in pixel value in a direction from the centre,
  - determining a distance from the centre where the most directions have a change in pixel value and determining the susceptibility from the distance, wherein the method further comprises:

- the step of determining the diameter comprises determining the change in a number of directions excluding directions toward neighbouring elements and/or
- the step of determining the diameter comprises determining the change in a number of directions excluding directions toward an edge of the carrier.

In the present context, susceptibility may depend on the type of cell/bacteria/microbe in question. Antibiotic susceptibility relates to the effect or efficiency which the antibiotic has on the microbe/bacteria. Antibiotic susceptibility may relate to the amount of antibiotic which will suffice to kill the microbe, such as within a predetermined period of time.

Susceptibility of a cell, such as a cancer cell, will correspondingly relate to the amount of the composition required to kill the cell or bring the cell to a state where it will no longer divide.

Antibiotic susceptibility often is quantified by providing the antibiotic in an element, such as a tablet, disc or wafer, and position it on a growth medium in which the microbe is allowed to grow. A circle will form around the element if the antibiotic has an effect on the microbe. The size of the radius or diameter of the circle will determine or represent the antibiotic susceptibility of the microbe to the antibiotic.

A similar method may be used for other cells which may also be provided in a medium and allowed to either divide or at least live. Then, the composition may be allowed to travel into the medium and thus kill cells if present in sufficient concentration and when the susceptibility is sufficiently high.

The carrier may be any type of carrier, such as a disc, such as a Petri dish. The carrier is preferably sterile before addition of the microbe. The medium preferably is a medium in which the microbe may grow and multiply. Standards exist as to the type and dimensions of the medium as well as how to apply the microbe. The element(s) are also usually applied in a standard manner. At least it may be preferred to ensure that the elements have a sufficient contact to the medium so that the antibiotic may travel into the medium. A frequently used test method is the Kirby-Bauer method.

One, two or more elements may be applied. Usually, different elements comprise different antibiotics or mixtures of antibiotics. Many standard elements are known. Such elements have specific IDs printed or applied thereon in order to be easily identified.

The elements may be wafers, tablets, discs or so-called antibiotic sensitivity disks. Elements preferably are porous or penetrable so that the antibiotic therein may exit the element and travel into and through the medium. The porosity, volume, height, diameter, penetrability of the element may be predetermined as may the amount of antibiotic therein.

In this context, an antibiotic may be any type of chemical, drug, composition or the like which has an effect on a microbe. Antibiotics may e.g. classified based on their mechanism of action, chemical structure, or spectrum of activity. Most target bacterial functions or growth processes. Those that target the bacterial cell wall (penicillins and cephalosporins) or the cell membrane (polymyxins), or interfere with essential bacterial enzymes (rifamycins, lipiarmycins, quinolones, and sulfonamides) have bactericidal activities. Protein synthesis inhibitors (macrolides, lincosamides, and tetracyclines) are usually bacteriostatic (with the exception of bactericidal aminoglycosides). Further categorization may be based on their target specificity. "Narrow-spectrum" antibiotics target specific types of bacteria, such as gram-negative or gram-positive, whereas broad-spectrum antibiotics affect a wide range of bacteria. Recently, four new classes of antibiotics have been brought into clinical use: cyclic lipopeptides (such as daptomycin), glycylcyclines (such as tigecycline), oxazolidinones (such as linezolid), and lipiarmycins (such as fidaxomicin).

Microbes in this aspect may be bacteria, fungi or the like.

Other types of cells may be used, such as cancer cells or other cells which are desired affected.

Components to which cells may be susceptible may be cancer drugs, chemotherapy drugs or the like. Examples of such drugs are: Cyclophosphamide, methotrexate, 5-fluorouracil, vinorelbine, Doxorubicin, cyclophosphamide, Docetaxel, doxorubicin, cyclophosphamide, Doxorubicin, bleomycin, vinblastine, dacarbazine, Mustine, vincristine, procarbazine, prednisolone, Cyclophosphamide, doxorubicin, vincristine, prednisolone, Bleomycin, etoposide, cisplatin, Epirubicin, cisplatin, 5-fluorouracil, Epirubicin, cisplatin, capecitabine, Methotrexate, vincristine, doxorubicin, cisplatin, Cyclophosphamide, doxorubicin, vincristine, vinorelbine, 5-fluorouracil, folinic acid, and oxaliplatin. Clearly, numerous other drugs are used also for other types of cancers.

When the antibiotic of the element(s) has/have been allowed to travel into the medium and the microbes have been allowed to grow, areas of the medium around the elements may have formed which differ from areas farther away by the fact that closer to the elements, the microbes have dies or not been present (the inhibition zone). Microbes will not be able to grow into areas with a too high concentration of an antibiotic to which they are sensitive.

It is noted that it may be desired to reverse the set-up so that the medium comprises the composition and the elements have therein the microbes/cells, especially when the microbes/cells are able to travel into the medium or will be able to multiply, so that new cells/microbes form in the medium. Also in this situation, circles will be formed.

When the elements are circular, the areas around them will be more or less circular. However, the areas of different elements may overlap, and some areas may reach an edge of the carrier. Thus, strictly circular areas cannot be expected.

Hitherto, such areas or radii/diameters have been determined manually with a ruler or other instrument. Automated processes have been developed but have not had the sufficient precision to take over the manual higher precision work.

According to the invention, an image is provided of at least part of the medium, the element(s) and the outline(s). In this respect, the image may be provided by a still camera, a video camera, a line scanner or the like. The image usually is a 2-dimensional representation of the medium etc. comprising a number, often in a matrix shape, of individual pixels or values representing a colour, intensity and/or grey value for each individual position in the image.

From the image, a diameter or radius is determined of the outline of the at least one element.

In one situation, the step of determining the diameter comprises determining the change in a number of directions excluding directions toward one or more neighbouring elements. All directions toward a neighbouring element may be excluded. A direction toward a neighbouring element may be straight directions from a centre of the element in question and toward any portion of the neighbouring element.

Directions toward neighbouring elements may be problematic in that overlap between the circles of the two neighbouring elements may be seen, whereby the distance to the change is not correct. Thus, if an overlap is seen, the direction(s) toward that neighbouring element may be left out. In fact, all directions toward an overlap may be discarded. Overlap may also be seen slightly to the side of the direction directly toward the neighbouring element. Thus, the method could exclude directions toward an overlap of a first area, which could be the circle, of pixel values (often different from those outside of the area) around the at least one element and a second area (circle) of pixel values around the neighbouring element. The pixel values of the two areas may be the same or different. The pixel values preferably are different, such as different colours and/or intensities, so that the overlap may be identified.

The overlap may have the shape of an oblong overlap between two circles each having a centre outside of the overlap.

In that or another situation, the step of determining the diameter comprises determining the change in a number of directions excluding directions toward an edge of the carrier. If the circle reaches the edge of the medium or carrier, the radius in that direction may not be correct. Thus, directions toward the nearest edge of the medium/carrier may also be excluded, such as if an estimate of the radius exceeds a distance from the element to that edge.

In one situation, the excluded directions are iteratively determined. Thus, a first estimate of the radii may be determined without excluding any directions. If an overlap is seen between circles or between a circle and an edge, corresponding directions may be excluded and a new estimate made. If this estimate alters a radius estimate, new overlaps may be determined which give rise to other directions to exclude, before another radius estimate is made. Thus, the excluded directions may be directions along which the distance to the edge is lower than the determined distance to the pixel variation (the radius), along one or more other directions, where this determined distance may be a mean distance or other distance determined over a number of directions not directed toward the edge.

In one situation, the step of determining the distance comprises, for each of a number of the directions:

- determining, along the direction and at least one adjacent direction, a distance from the centre to the determined change,
- determining a difference in the distance for the two directions, and
- allocating a higher weight for a lower difference, wherein the step of determining the distance comprises determining the distance from the centre from the distances and weights for the number of directions.

In this situation, the distances may be at angles, around a centre of the element, from a predetermined initial angle, such as toward a centre of the carrier. Directions may be determined at predetermined angles or with a predetermined angle interval, such as each degree, each half degree, every 5 degrees or whatever is desired.

Adjacent directions are the neighbouring directions, so that if directions are made for each degree, the direction at 3 degrees would have neighbouring directions at 2 and 4 degrees.

When neighbouring directions have changes at the same or almost the same distance, that distance is more reliable than if very different distances were seen.

Thus, the lower the difference in the distances of neighbouring directions, the higher weight may be allocated to that distance, as it may be seen as more reliable.

Naturally, the weight may be directly inversely proportional to the difference, or any other relation may be used. In a simple example, a low and a high weight may be used where the difference is below or above a threshold value, for example.

In that or another situation, the step of determining the distance comprises, for each of a number of the directions:

- determining, along the direction and at least one adjacent direction, a distance from the centre to the determined change,
- determining a number of adjacent directions, the distance of which are within a threshold distance from the distance of the pertaining direction.
- allocating a higher weight for a lower difference, and wherein the step of determining the distance comprises determining the distance from the centre from the distances and weights for the number of directions.

In this situation, the number of adjacent (neighbouring) directions may determine the weight. The more adjacent directions, such as an unbroken series of adjacent directions, which have a distance within the threshold distance, or within a distance interval, the higher the weight, as a large number of directions will increase the credibility of that distance as the correct distance.

Again, the number of adjacent directions may be correlated directly to the weight. Alternatively or additionally, the threshold distance or the width of the distance interval within which the distances of the directions lie, may be correlated to the weight.

In a particularly interesting embodiment, the step of providing the carrier comprises providing the carrier with the medium comprising microbes and the elements comprising antibiotics. In that situation, the method may be that of an antibiotic susceptibility test (AST).

Another aspect of the invention relates to a system for determining susceptibility, the system comprising:

- a carrier with:
  - a medium comprising one of
    - bacteria or cells or
    - a composition affecting the bacteria or cells
  - a plurality of elements each comprising the other of the composition or the bacteria/cells, at least a portion of an outline formed around at least one element,
- an imaging element configured to provide an image of the carrier with the plurality of elements, the image having a number of pixels each having a pixel value,
- a controller configured to determine a diameter of the outline of at least one element by:
  - in a plurality of directions from a centre of the element:
    - determining a change in pixel value in a direction from the centre, and
  - determining a distance from the centre where the most directions have a change in pixel value and determining the susceptibility from the distance, wherein the controller is configured to, during the step of determining the diameter, determine the change in a number of directions excluding directions toward neighbouring elements and/or a number of directions excluding directions toward an edge of the carrier.

Naturally, the carrier may be replaceable, and a number of carriers may be used, such as sequentially, in the system. Often, carriers are class receptacles, such as Petri dishes, or the like which may be sterilized between uses.

The medium, cells, components, bacteria, micro organisms and the like may be as described above.

All embodiments, situations or the like of the above aspect of the invention are equally relevant in this and all other aspects of the invention.

Actually, the system is not required to comprise the carrier. It suffices that the system is capable of providing the image, such as when the system has a surface configured to support the carrier while the imaging element provides the image.

The imaging element may be any type of camera, such as a still camera, video camera, scanning camera or the like. The image may have any format. Usually, images are 2D representations of what the camera sees. Thus, the circles, elements may be seen as well as, preferably, the edge of the carrier and/or medium.

Usually, images are formed by or are represented by a number of positions, often called pixels, each of which relates to a particular portion of the carrier/element/medium or the like, and each of which has one or more values describing a colour, intensity, grey value or the like.

The controller is configured to receive the image from the camera. Naturally, pre-processing may be performed if desired. For example, the below-mentioned thresholding may be performed in the camera, the controller or between these by a separate element if desired.

The controller may be any type of controller, processor, FPGA, DSP or the like. It may be software controlled or hardwired. Actually the controller may be formed by a number of such elements which then may be configured to communicate with each other via or without wires/fibres.

The controller is configured to determine the diameter of the outline of at least one element. Naturally, the controller may also handle other operations, such as controlling of the camera. The camera may be controllable in a number of manners, such as the shutter time, the size of an aperture thereof, any post processing as well as when to take an image—or how many images to take.

The controller is also capable of determining the directions in the image from a centre of the element. This may be performed for each element or multiple elements in the image.

Determining the presence of an element may be performed by e.g. knowing the approximate size and/or shape of the element and then searching in the image for portions having that size/shape. A filter with that size/shape may be generated and moved across the image in order to identify potential elements. Then, finding the centre of the element may be performed in any of a wide variety of manners, depending on the shape of the element.

The directions may, as is described above, be straight lines from the centre and outwardly therefrom and at determined angles, such as relative to an initial angle, or which have a predetermined angular difference, such as 1 degree, ½ degree, 5 degrees or what is desired.

A change in pixel value may be a change in intensity, colour, grey value or the like. Any combination may be used. The change may be made more easily determined if the image is noise reduced or pre-processed in different manners, such as by removing small inclusions of pixels which may be assumed to not relate to the edge of the circle, or by thresholding or otherwise filtering the image to bring forward the change looked for.

In this context, a change is a variation along the direction. Thus, closer to the element, the pixels will have one value (or one type of values) and farther away, seen from the change, the pixels will have the other value(s).

The distance thus is determined from the directions having more or less the same distance, as it is assumed that the outline looked for is more or less circular.

The susceptibility is determined from the distance which will relate to the radius or diameter of the circle.

In one situation, the controller is configured to, during the step of determining the diameter, determine the distance to the change in a number of directions excluding directions toward neighbouring elements. As mentioned above, the distance in these directions may be erroneous as an overlap may be seen. Then, directions may be excluded toward an overlap of a first area of pixel values around the at least one element and a second area of pixel values around the neighbouring element.

In one situation, the controller is configured to, during the step of determining the diameter, determine the distance to the change in a number of directions excluding directions toward an edge of the carrier. As described above, the circle may reach the edge of the carrier or medium so that the radius in this direction is erroneous. The excluded directions may be directions along which a distance to the edge is lower than a determined distance, along one or more other directions.

In one embodiment, the controller is configured to iteratively determine the excluded directions. This is described further above.

In one embodiment, the controller is configured to, during the step of determining the distance, for each of a number of the directions:

- determine, along the direction and at least one adjacent direction, a distance from the centre to the determined change, determine a difference in the distance for the two directions, and allocate a higher weight for a lower difference, wherein the step of determining the distance comprises determining the distance from the centre from the distances and weights for the number of directions. This is described further above.

In one embodiment, the controller is configured to, during the step of determining the distance, for each of a number of the directions:

determine, along the direction and at least one adjacent direction, a distance from the centre to the determined change, determine a number of adjacent (unbroken) directions, the distance of which are within a threshold distance from the distance of the pertaining direction.

allocate a higher weight for a lower difference, and wherein the step of determining the distance comprises determining the distance from the centre from the distances and weights for the number of directions. This is described above.

In a particularly interesting embodiment, the medium comprises microbes and the elements comprising antibiotics. Then, the system may be a device for use in an antibiotic susceptibility test (AST).

In the following, preferred embodiments of the invention will be described with reference to the drawing, wherein.

The present technology may be embodied in different manners. Below is an antibiotic susceptibility test described where the medium comprises bacteria or microbes and the elements different antibiotics or compositions. In this situation, the antibiotics will exit the elements and travel into the element and thus provide inhibition zones, the radii of which describe the susceptibility of the microbes to the individual antibiotics.

Alternatively, the medium may comprise an antibiotic or composition and the elements bacteria or microbes. In this situation, the bacteria/microbes may grow out of the elements and into the medium. Again, inhibition zones will be defined by now from outside and toward the elements and not in the opposite direction.

Clearly, the technology may also be used on other types of elements, such as cells. The medium may comprise therein cancer cells or other types of cells. Then, the elements may comprise different types of drugs aimed at killing the cancer cells.

Figure 1:
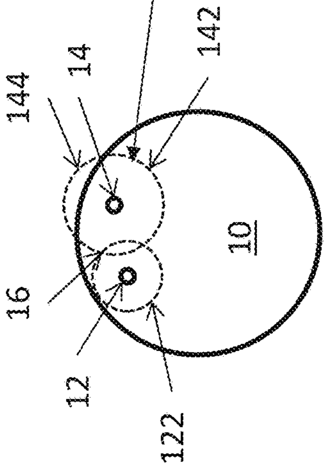
FIG. 1 illustrates a Petri dish comprising two tablets with an antibiotic.

In FIG. 1, a Petri dish 10 is illustrated in which a bacteria or microbe has been grown on a growth medium, such as Agar. Before the growth phase, two discs/tablets 12, 14 comprising an antibiotic have been positioned on the growth medium. As is known, the antibiotic will prevent the growth of the bacteria in the medium.

Depending on the susceptibility of the bacteria to the antibiotic, a circle of a certain diameter will be generated around the disc. This is called the "inhibition zone". The larger the diameter, the larger the susceptibility. Thus, the diameter is desired determined.

However, an overlap 16 may be seen between the circles 122, 142 of the discs. In addition, the circles may reach the edge of the petri dish so that the apparent diameter is lower than the real diameter. This is seen at the portion 144.

Thus, from such incomplete data, the diameter is nevertheless desired determined.

Figure 4:
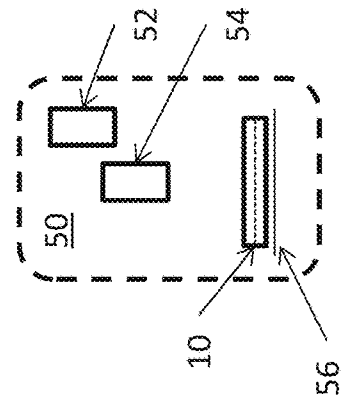
FIG. 4 illustrates a system for performing the determination.

FIG. 4 illustrates a system for determining these radii. The system 50 has a surface 56 for supporting the carrier etc. while a camera 54 provides an image. A processor 52 receives the image and performs the below analysis.

Determination of the radius or diameter of the circle (inhibition zone) of a disc is performed by, for a number of directions from a centre of the disc, determining the grey values or colours as a function of the distance to the centre.

Figure 3:
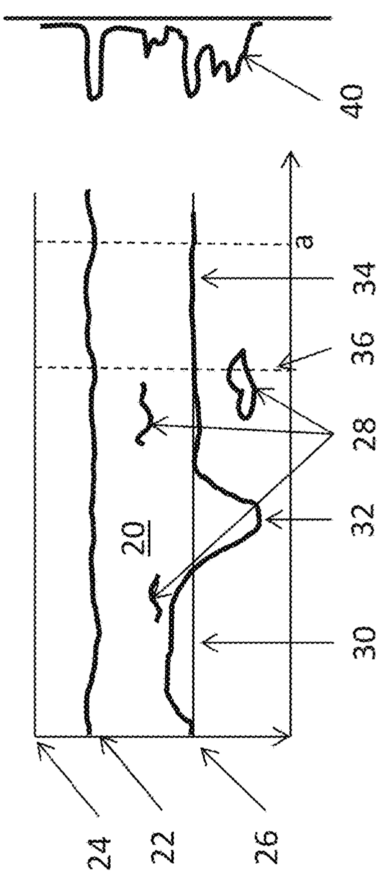
FIG. 3 illustrates a manner of determining the radius.

These plots may be provided as illustrated in FIG. 3, where the distance is in the vertical direction and the angle of the pertaining direction is in the horizontal direction.

Figure 2:
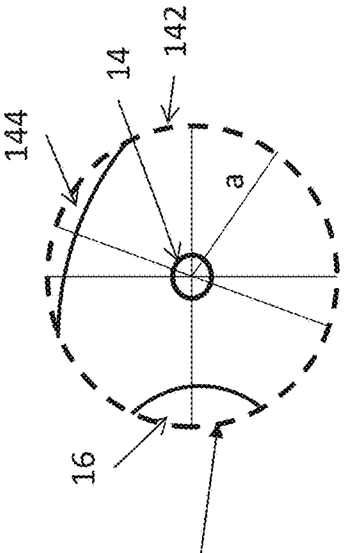
FIG. 2 illustrates a plot indicating the edges.

The angle may be determined from any initial angle, such as horizontally in the image. In FIG. 3, the initial angle (starting to the left in the plot 20) is horizontally to the right of the centre (3 o'clock), and the angle is rotated counter clockwise. Thus, different horizontal positions in the plot of FIG. 3 will correspond to the image of FIG. 2 at different angles. For example, the line a in FIG. 2 is illustrated in the position a in FIG. 3.

In this plot 20, a number of grey tone (or colour or intensity) edges or variations are visible. Naturally, an edge of the disc 14 is seen which for a circular disc will be an edge 22 which is at least substantially equidistant from the centre (top line 24) of the disc. In this plot, distance is downward, as the centre of the disc is at the top.

Also, the edge of the circle 142 may be seen. It is seen that in a portion 30 thereof, the apparent distance from the disc centre 24 to the circle edge is lower than at other portions. This is due to the interference of the edge of the disc 10—i.e. the portion 144.

At other portions, the distance seems larger than at other portions, such as at the portion 32.

This is in the direction of the disc 12, so that at least a portion of the larger distance is created by the overlap of the circles 122 and 142.

At other portions, such as portion 34, there are no particular disturbances so that this distance may be more accurate or less error prone than the distance at the portions 30 and 32.

A number of manners may now be used for estimating the correct radius.

The curves 22 and 26 illustrate the edge of the disc 14 and the edge of the circle 142 with the alterations thereof caused by the edge of the disc 10 and the circle 122. These lines may be derived from variations in colour, grey value, intensity or the like in the plot 20 or in the image. Thus, the image or the plot may be thresholded or the like to detect such changes.

Clearly, a thresholding of this type may also bring other features out, such as noise or variations in the medium on the disc 10. Thus, noise edges 28 may also be seen in the plot. Naturally, these elements will present a challenge for the determination of the circle radius or diameter.

Noise may be reduced by identifying and deleting portions of the plot which are too small. Groups of interconnected pixels may be identified and groups with a size or area/length below a limit may be deleted. In this manner, the smaller noise elements in the plot may be deleted.

One manner of determining the radius is indicated to the right in FIG. 3. The curve 40 may be derived by summing the number of pixels or directions or grey tones along horizontal lines. In this manner, a peak will be seen at vertical positions having larger portions of horizontal portions of the curve 26. The noise clearly will also be part of this curve 40, but as it would be stochastically positioned in the plot 20 and have any angles and extensions, its influence will be reduced.

From the plot 40, the lower, high, peak identifies a horizontal line at the more horizontal portion 34 of the curve 26. This corresponds to the radius of the circle 142.

It is seen that the portions 30 and 32 are less influential using this method.

In that or other methods, the portions 30 and 32 may be discarded before determining the radius. In one situation, all directions toward a neighbouring disc 12 may be discarded as they potentially may have an overlap and thus an erroneous radius. Also, directions toward the nearest portions of the disc edge may be discarded, as also they may be erroneous.

Naturally, this discarding may be iterative, so that a direction toward a neighbouring disc is only discarded if the combined first estimates of the radii of the two circles exceed a distance between the two discs. If the combined radii exceed the distance, an overlap will be seen, and it may then be calculated for each disc the directions within which the circles overlap.

Similarly, directions toward the disc edge which are to be discarded may depend on the first estimate of the radius 142 and the lowest distance from the edge of the disc 14 to the disc edge. If the radius exceeds this lowest distance, it is easy to calculate which directions from the disc are then to be discarded: those along which the radius reaches the disc edge.

Naturally, a re-iteration may well change these directions again, but the calculation will converge.

The resulting plot may then be one without the portions 30 and 32.

Another simple manner of arriving at an enhancement of the precision of the determination is to allocate different weights to different portions of the plot. Thus, the position 36, being a direction directly toward a centre of the disc 10, may be allocated a relatively high weight especially in situations where no discs are positioned between the disc 14 and the centre of the disc.

Portions 30 and 32 may then be allocated a lower weight, as they are at directions toward the disc edge and/or toward a neighbouring disc. This lower weight may be allocated to directions toward the edge/disc or to portions deviating sufficiently from more horizontal portions, such as portion 34.

In another manner, horizontal portions of plot 20 may be given prevalence over other portions, such as by allocating to each portion (such as an angle interval) a weight corresponding to this portion's angle to horizontal. The more horizontal, the higher the weight.

One manner of obtaining this is to drive a filter over the plot, the filter having a long and narrow window which is horizontal. A larger weight will be given to portions with larger portions thereof inside the filter window.

Clearly, the transition from inside a circle to outside of the circle may not be very sharp. The boundary between living and dead bacterial will be seen over a certain distance.

Then, the determination of the radius may be made from the inner most portion of the circle, where there still are living bacteria, or from the outermost portions where a few dead bacteria are seen. Clearly, this may be obtained using the thresholding or the manner in which the distance for each direction is determined. Different such distance determinations may be desired for different uses, so different standards may relate to different positions in the transition between ~100% dead bacteria and ~100% living bacteria.

From the radius found, the susceptibility of the bacteria to the antibiotic in the disc may be determined.

Clearly, different radii will mean different susceptibility, but it may be desired to calibrate the measurement, as the radii may vary with the thickness of the medium on the disc, the amount of bacteria per area in the medium as well as how fast the antibiotic travels out of the disc and into the medium.

The invention claimed is:

1. A method, comprising:
- providing a carrier, the carrier including
  - a medium comprising cells, and
  - a plurality of porous elements each comprising a composition affecting the cells, such that an outline is formed around at least one porous element of the plurality of porous elements in the medium based on the composition affecting the cells in the medium,
- providing an image of the carrier with the plurality of porous elements and the medium, the image including a plurality of pixels, each pixel of the plurality of pixels having a respective pixel value,
- determining a diameter of the outline formed around the at least one porous element by determining,
  - in a plurality of directions from a centre of the at least one porous element in the image,
    - a respective distance from the centre to a change in pixel value in each respective direction of the plurality of directions from the centre, and
  - a distance from the centre where the most directions have the change in pixel value in the image and determining a susceptibility of the cells to the composition based on the distance,
- wherein the step of determining the diameter includes determining respective distances from the centre to the change in pixel value in a number of directions, excluding
  - distances from the centre to the change in pixel value in directions toward one or more neighbouring porous elements, and
  - distances from the centre to the change in pixel value in directions toward an overlap of a first area of pixel values around the at least one porous element and a second area of pixel values around a neighbouring porous element of the plurality of porous elements.

2. The method according to claim 1, wherein the excluded directions toward an edge of the carrier are directions along which a distance to the edge is lower than a pre-determined distance.

3. The method according to claim 1, wherein the excluded directions are iteratively determined.

4. The method according to claim 1, wherein the step of determining the distance comprises, for each pertaining direction of a number of directions of the plurality of directions:
- determining, along the pertaining direction and at least one adjacent direction, a distance from the centre to the determined change in pixel value,
- determining a difference in the distance for the pertaining direction and the distance for the at least one adjacent direction, and
- allocating a higher weight for a lower difference,
- wherein the step of determining the distance comprises determining the distance from the centre from the distances and weights for the number of directions.

5. The method according to claim 1, wherein the step of determining the distance comprises, for each pertaining direction of a number of directions of the plurality of directions:

determining, along the pertaining direction and at least one adjacent direction, a distance from the centre to the determined change in pixel value, determining a number of adjacent directions, the distance of which are within a threshold distance from the distance of the pertaining direction, and allocating a higher weight for a greater number of adjacent directions, wherein the step of determining the distance comprises determining the distance from the centre from the distances and weights for the number of directions.

6. The method according to claim 1, wherein the step of providing the carrier comprises providing the carrier with the medium and the plurality of porous elements, the medium comprising microbes, and the plurality of porous elements comprising antibiotics.

7. The method according to claim 1, wherein the cells include bacteria.

8. The method according to claim 1, wherein the step of determining the diameter includes determining respective distances from the centre to the change in pixel value in the number of directions, further excluding distances from the centre to the change in pixel value in directions toward an edge of the carrier.

* * * * *